United States Patent
Williams et al.

(10) Patent No.: US 9,115,945 B2
(45) Date of Patent: *Aug. 25, 2015

(54) APPARATUS AND METHOD FOR CLEANING THE BARREL OF A FIREARM

(71) Applicant: Otis Products, Inc., Lyons Falls, NY (US)

(72) Inventors: Nicholas Williams, Naples, FL (US); James R. Brooker, Constantia, NY (US)

(73) Assignee: Otis Products, Inc., Lyons Falls, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/785,966

(22) Filed: Mar. 5, 2013

(65) Prior Publication Data

US 2014/0123529 A1    May 8, 2014

Related U.S. Application Data

(60) Provisional application No. 61/724,012, filed on Nov. 8, 2012.

(51) Int. Cl.
*F41A 29/00* (2006.01)
*F41A 29/02* (2006.01)

(52) U.S. Cl.
CPC ..................................... *F41A 29/02* (2013.01)

(58) Field of Classification Search
CPC ................. F41A 29/00; F41A 29/02
USPC ......... 42/95, 96; 15/104.05, 104.16, 104.165, 15/104.17, 104.18, 104.19
See application file for complete search history.

(56) References Cited

U.S. PATENT DOCUMENTS

| 486,331 | A | * | 11/1892 | Garrion | 15/104.19 |
|---|---|---|---|---|---|
| 904,122 | A | * | 11/1908 | Fletcher | 15/104.19 |
| 940,985 | A | * | 11/1909 | Moore | 15/104.19 |
| 1,164,665 | A | * | 12/1915 | Reeves | 15/104.16 |
| 1,172,746 | A | * | 2/1916 | Silverstein | 15/104.16 |
| 1,213,383 | A | * | 1/1917 | Kiessig | 15/104.165 |
| 1,516,438 | A | * | 11/1924 | Inskip | 15/104.16 |

(Continued)

FOREIGN PATENT DOCUMENTS

CH        692825 A5 * 11/2002 ............. F41A 29/02

OTHER PUBLICATIONS

Danish Patent and Trademark Office Search Report for Corresponding Turkish Application No. 2013/12857 dated May 15, 2015 (7 pgs).

*Primary Examiner* — Gabriel Klein
(74) *Attorney, Agent, or Firm* — Harris Beach PLLC (57) ABSTRACT

A device for cleaning the barrel of a firearm comprising a longitudinal central member having a leading end and a trailing end; a tubular woven sheath surrounding said central member; and a radial protrusion formed of a polymer disposed about said central member and under the tubular woven sheath. The radial protrusions are overmolded thermoplastic that distends the sheath radially to the internal diameter of gun barrel. The central member may include a fitting for attachment to various auxiliary tools or a T-handle. The surface of the polymer is provided with helical pattern of protrusions formed to urge the sheath against the lands of barrel rifling. The sheath is woven of primarily a natural fiber such as cotton. Luminescent, abrasive or heat resistant threads may also be woven into the sheath. A sponge material may be disposed between the sheath and the central member.

18 Claims, 7 Drawing Sheets

(56) References Cited

U.S. PATENT DOCUMENTS

| | | | |
|---|---|---|---|
| 1,525,933 A * | 2/1925 | Haigh | 15/104.165 |
| 3,064,294 A | 11/1962 | Stocking | |
| 3,100,904 A | 8/1963 | Stocking | |
| 3,682,556 A * | 8/1972 | Hanson | 401/132 |
| 3,708,820 A | 1/1973 | Schultea | |
| 3,765,045 A | 10/1973 | Schneider et al. | |
| 4,010,565 A | 3/1977 | DiProspero | |
| 4,222,142 A | 9/1980 | DiProspero | |
| 4,344,278 A | 8/1982 | Jamison et al. | |
| 4,509,223 A | 4/1985 | Sipple et al. | |
| 4,606,183 A | 8/1986 | Riggs | |
| 4,716,673 A * | 1/1988 | Williams et al. | 42/95 |
| 4,962,607 A * | 10/1990 | Baldwin | 42/95 |
| 5,171,925 A | 12/1992 | Mekler | |
| 5,357,705 A | 10/1994 | Stengel | |
| 5,588,242 A | 12/1996 | Hughes | |
| 5,871,589 A | 2/1999 | Hedge | |
| 5,934,000 A | 8/1999 | Hayes, Sr. | |
| 5,972,125 A | 10/1999 | Hedge | |
| 6,389,978 B1 * | 5/2002 | Hooper et al. | 102/442 |
| 6,630,034 B1 | 10/2003 | Schnell | |
| 6,640,480 B2 | 11/2003 | Williams et al. | |
| 7,356,961 B2 | 4/2008 | Williams | |
| 8,176,592 B1 * | 5/2012 | Carpenter et al. | 15/104.165 |
| 8,186,092 B2 | 5/2012 | Williams | |
| 8,250,800 B1 | 8/2012 | Johnson | |
| 8,371,441 B2 | 2/2013 | Williams | |
| 8,448,370 B2 | 5/2013 | Williams | |
| 8,567,107 B1 * | 10/2013 | Bascue et al. | 42/95 |
| 2004/0159331 A1 * | 8/2004 | Katsin | 134/6 |
| 2006/0162223 A1 * | 7/2006 | Whipple | 42/95 |
| 2006/0288625 A1 | 12/2006 | Williams | |
| 2009/0283115 A1 * | 11/2009 | Dentico | 134/22.1 |
| 2011/0099880 A1 * | 5/2011 | Stephens et al. | 42/95 |
| 2012/0198747 A1 | 8/2012 | Niebling | |

* cited by examiner

APPARATUS AND METHOD FOR CLEANING THE BARREL OF A FIREARM

The present application draws priority from a provisional U.S. Provisional patent application, Ser. No. 61/724,012, filed Nov. 8, 2012.

FIELD OF THE INVENTION

The present disclosure relates generally to a system and tools for cleaning the interior of tubular members. More particularly, the disclosure relates to a tool comprising a central core supporting a region of overmolded elastomer around the cable core. The system may also include a tubular woven sheath surrounding at least a portion of the overmolded elastomer. The central core may include a fitting at one end and preferably at both ends for attachment to any of various auxiliary tools such as swabs, brushes, scrapers, handles, adapters and the like. The present disclosure also relates to a system and tools for the cleaning of the barrels of firearms such rifles, carbines, pistols.

BACKGROUND OF THE INVENTION

Relatively narrow tubular members are inherently difficult to clean. Process fluids may contain impurities that are be deposited on the interior surface of a tubular member. Smaller diameter piping, drains, conduit and tubing may also have turns around which rigid rods and brushes may not be able to reach to scrub loose accumulated deposits. Heat, humidity and pressure may affect the rate and thickness of accumulated deposits.

The barrels of firearms are one form of tubular members that are difficult to clean. Carbon and other residue from gunpowder and from firearm discharge reactions accumulate in firearm barrels, with deleterious effects on cleanliness, performance, and longevity of the firearm. Such residues require partial disassembly of a weapon to access and clean the barrel and associated firing chamber. A number of specialized swabbing, brushing and scraping tools have been introduced to clean firearm components, but have had substantial shortcomings.

U.S. Pat. No. 4,716,673 discloses a gun barrel cleaner comprising an elongated flexible shaft having a universal coupling secured to each opposite end and several different cleaning tips selectively threadably and detachably engageable with either universal coupling. One cleaning tip, a gun barrel bore obstruction remover, comprises a cylindrical body portion having a concave face at one end and securing means at the other end for attaching the tip to the shaft. A compact cylindrical container for storing and conveniently transporting the gun barrel cleaner is provided. In addition, an improved method of attaching a cleaning patch to a gun barrel cleaning tip having a patch receiving slot is provided.

A disadvantage of this invention is that the cleaning patch is not integral with a brush or a scrubbing element of the tool. Therefore, cleaning operations will generally require more than a successive passes of the gun barrel cleaner through the barrel. For example, a first pass of the tool may include a slotted tip with a swab wetted with an appropriate solvent; a second pass may include a pulling an appropriately sized bore brush; a third pass may include a clean swab pulled through the barrel to absorb the dislodged residue; and a fourth pass may include pulling another swab wetted with a preserving lubricant U.S. Pat. Nos. 5,871,589 and 5,972,125 disclose a cleaning tool for cleaning the inside of gun barrels. The device consists of a metal brush which is enclosed within a tubular sheath of material, typically a woven fabric. The bristles of the brush extend through the wall of the woven sheath of fabric. The tubular sheath is pulled through a gun barrel and the bristles of the brush clean the inside of the gun barrel. Also enclosed within the tubular sheath are one or more foam inserts, or one or more cleaning regions formed by folding the cord within itself, either of which creates a bulge in the tubular sheath and cleans debris from the gun barrel, spreads gun cleaning solvent in the gun barrel, absorbs solvent and combustion and bullet residues, and spreads a layer of gun oil in the gun barrel.

A shortcoming of the device disclosed in both patents is that an attached flexible cord for pulling the sheath through the barrel does not extend throughout the length of the sheath. Because the sheath is longitudinally stretchable, the device can jam in a firearm barrel and become difficult to remove. Further, the preferred material of the sheath is a synthetic polymer that is not as absorbent as a natural fiber such as cotton, resulting in less effective presentation of cleaning solvent and/or lubricant against the surface of the barrel, which effect is compounded by a reduction in effective diameter of the sheath under tension. Once jammed, excessive tensile force on the flexible lead cord may result in a failure of the cord, the synthetic sheath or the sewn connection therebetween. As the flexible cord lacks a semi-rigid core, it is frequently difficult to feed or thread the flexible cord through the tubular member, particularly when the bore of the tube or gun barrel is partially obstructed by mud, debris, an excessive accumulation of carbon residue, or a combination thereof. Consequentially, a further disadvantage is that the flexible shaft does not comprise an integral gun barrel obstruction remover. Further, no fitting is provided at the leading or trailing end of the sheath for attachment of auxiliary cleaning tools as may be desirable.

SUMMARY OF THE INVENTION

Briefly described, an apparatus for cleaning the barrel of a firearm or other tubular member comprises a tubular woven sheath having a lead end and a trailing end as defined by passage of the apparatus through a gun barrel. A central core which is substantially unyielding in the axial direction for gun barrel cleaning is disposed within the woven sheath. In one aspect of the invention, the central core comprises a cable of twisted strands of metal or non-metallic material. Alternatively, the central core may comprise a single filament, wire, or a woven or extruded cord of metal or non-metallic material. The sheath extends over a substantial part of the central core and, preferably, extends beyond one or both ends of the sheath. A region of the central core beneath the sheath is overmolded with a thermoplastic elastomer that radially distends the sheath to approximately the diameter of a specific caliber gun barrel to be cleaned. The thermoplastic elastomer is slightly compressible to reduce the risk of any jamming of the gun barrel cleaner within the barrel. The central core includes a fitting at one end and preferably at both ends for attachment to any of various auxiliary tools such as swabs, brushes, tips, scrapers, a T-handle, and the like, as well as an extender. The fittings may be crimped, bonded or cold welded to the central core ends and may include male or female threads or quick release mechanism complementary to the fittings of the auxiliary tools. Preferably, the outer surface of the elastomer region is provided with patterned protrusions that urge the sheath into the rifling in the barrel bore. Preferably, the protrusions are formed to urge the sheath and central core to twist along the lands of the rifling. In one embodiment, the protrusions are discontinuous ridges that follow a helical line that is complementary to the helical rifling on the interior of the gun barrel.

Preferably, the sheath is woven of primarily a natural fiber such as cotton. Additional special-purpose threads, such as fiber-optic, luminescent or phosphorescent threads, heat resistant materials and/or staple set formed textured threads, may also be woven into the sheath. In another aspect of the invention, one or more sections of additional absorbent material, such as a thin cylindrical sponge, may also be disposed within the sheath, preferably at the lead end thereof, ahead of the overmolded thermoplastic region for the application of cleaning solvent.

According to one aspect, the invention features a device for cleaning the barrel of a firearm comprising a central member defining a core and having a longitudinal length, a leading end and a trailing end; a tubular woven sheath surrounding said central member and having a lead end and a trailing end; and a radial protrusion formed of a polymer disposed about said central member between said central member and said tubular woven sheath.

In one embodiment of the gun barrel cleaning device, the central member is selected from the group consisting of rope, cord, rod, wire, twisted cable, and braided cable.

In yet another embodiment, the central member further comprises is a metal cable.

In yet another embodiment, the central member further comprises a protective coating In yet another embodiment, the central member has a fitting at one end adapted to attach an auxiliary tool selected from the group consisting of brushes, scrapers, tips, swabs, handles, adapters and extender cables.

In yet another embodiment, the tubular woven sheath comprises a natural fiber.

In yet another embodiment, the tubular woven sheath further a fiber of abrasive materials selected from the group consisting of nylon, polystyrene, acetals, acrylics, and brass.

In yet another embodiment, the tubular woven sheath comprises heat resistant materials selected from the group consisting of meta-aramids, NOMEX, para-aramids, KEVLAR, fiberglass, and K-fiber.

In yet another embodiment, the tubular woven sheath includes a fiber selected from the group consisting of fiber-optic, luminescent and phosphorescent to provide for auxiliary lighting for visual inspection of said gun barrel.

In yet another embodiment, the sheath further comprises staple set formed textured threads.

In yet another embodiment, the sheath is retained over the apparatus by the tight fit of the tubular woven sheath over the radial protrusions.

In yet another embodiment, the woven tubular woven sheath further comprises elasticized threads to assist in the removal and replacement of the tubular woven sheath over the device.

In yet another embodiment, the outer diameter of said radial protrusion is approximately equal to a diameter of the bore of said gun barrel.

In yet another embodiment, the radial protrusion is formed of a thermosetting rubber polymer.

In yet another embodiment, the radial protrusions are formed by overmolding onto said central member.

In another embodiment of the gun barrel cleaning device, there are a plurality of radial protrusions molded over the central member.

In yet another embodiment, the radial protrusions form discontinuous ridges

In yet another embodiment, adjacent radial protrusion are disposed in progressive angular rotation about said central member.

In yet another embodiment, the radial protrusion is helically oriented along the longitudinal length of said central member.

In yet another embodiment, the helical orientation of said radial protrusion in the same direction as a rifling within said gun barrel.

In yet another embodiment, the plurality radial protrusions urge the sheath to engage rifling lands within in the gun barrel.

In yet another embodiment, the central member is formed with a natural curl to promote laterally coiling in storage.

In another embodiment, the gun barrel cleaning device further comprises absorbent material disposed between said central member and said tubular woven sheath.

In yet another embodiment, the gun barrel cleaning device further comprises a crimping ring to attach the sheath to the central member.

In yet another embodiment, the crimping ring retains a leading edge of the sheath in place over the central member.

In yet another embodiment of the invention, a device for cleaning tubular member comprises a central member defining a core having a leading end and a trailing end and an overmolded polymer profile comprising a plurality of radial protrusions. The radial protrusions are preferably helically displaced about the polymer profile to wipe fluids and semi-solids from the interior of the tubular member. The helical radial protrusions may be discontinuous to prevent over-accumulation of dislodged residue that might otherwise jam the cleaning tool within the tubular member.

BRIEF DESCRIPTION OF THE DRAWINGS

The features described herein can be better understood with reference to the drawings described below. The drawings are not necessarily to scale, emphasis instead generally being placed upon illustrating the principles of the invention. While the particular embodiments are described in relation to cleaning the interior of a gun barrel, individuals skilled in the art will recognize and understand that the disclosure and embodiments herein are equally applicable to cleaning pipes, conduits and tubing that is both straight and curved. In the drawings, like numerals are used to indicate like parts throughout the various views.

DETAILED DESCRIPTION OF THE INVENTION

Figure 1:
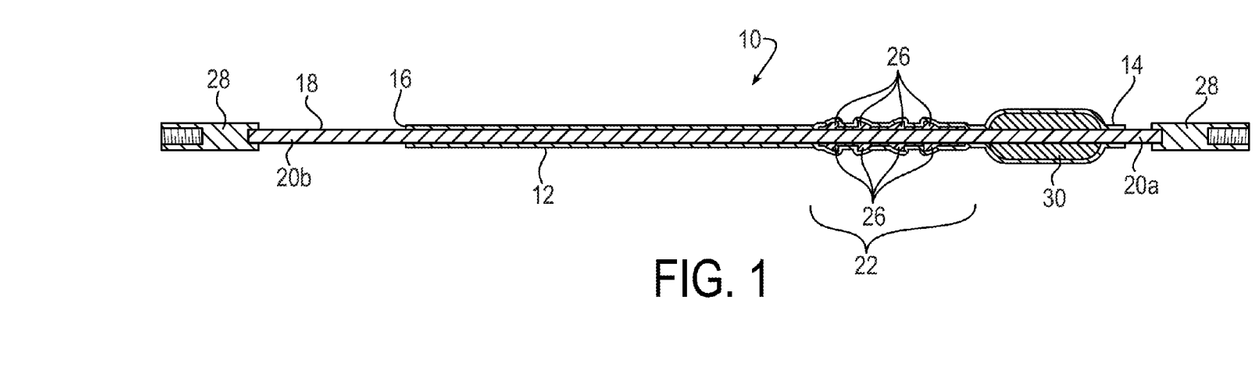
FIG. 1 is a longitudinal cross-sectional view of a gun barrel cleaning apparatus in accordance with the present invention.
Figure 2:
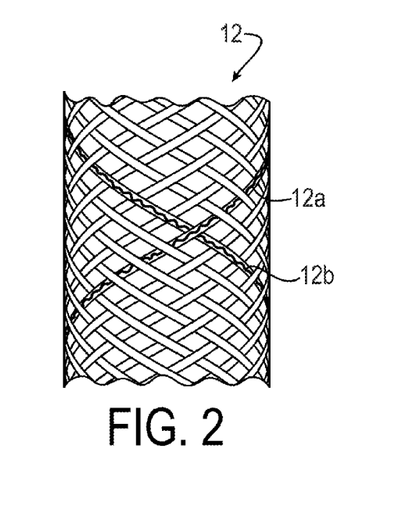
FIG. 2 is an elevational view of a portion of a tubular woven sheath in accordance with the present invention.

Referring to FIGS. 1 and 2, an apparatus 10 (also referred to herein as a "tool" or "gun barrel cleaner") for cleaning the barrel of a weapon or other tubular member comprises a tubular woven sheath 12 having a lead end 14 and a trailing end 16 as defined by passage of the apparatus through the barrel. Tool 10 may be passed through a barrel in either direction although it is preferable to pass the tool from the firing chamber toward the muzzle of the barrel to reduce the accumulation of dislodged residue in the firing and loading mechanisms within the chamber and receiver of the firearm and reduce the incidence of failure of such mechanisms. An elongate central member 18 defines a core disposed within tubular woven sheath 12 and generally extending the length of sheath 12 and, in one embodiment, some length 20a, 20b beyond one or both ends of sheath 12.

Figure 4A:
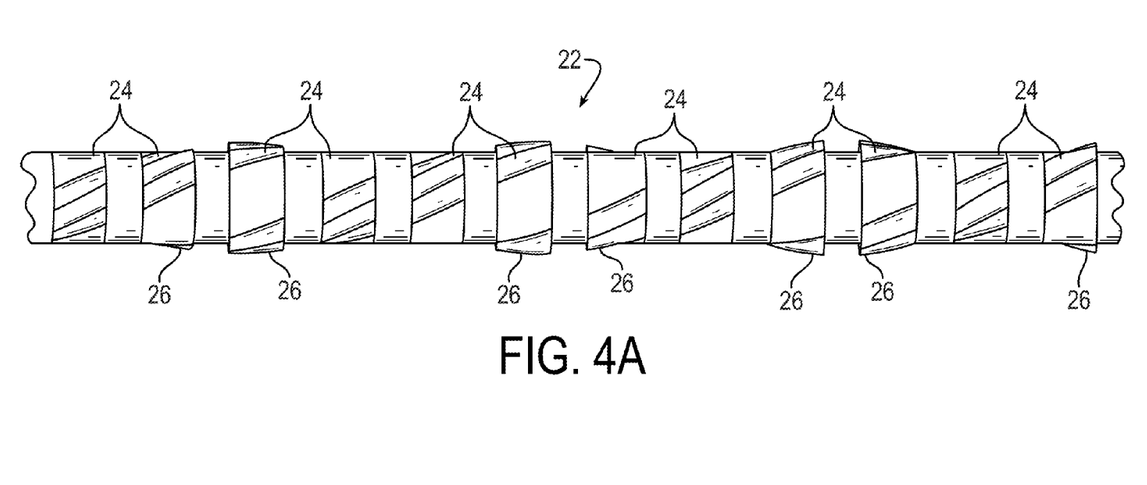
FIG. 4A is an elevational view of a portion of the apparatus shown in FIG. 1 showing a central core having a feature comprising a plurality of radial protrusions.
Figure 4B:
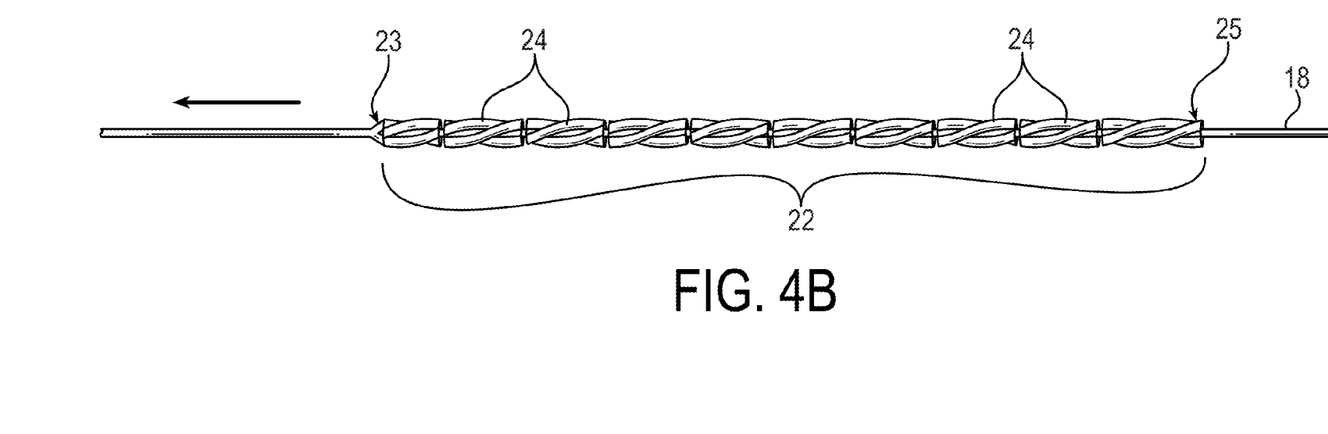
FIG. 4B is an elevational view of another embodiment of the portion of the apparatus shown in FIG. 4A comprising a central core having an overmolded plurality of helical radial protrusions.
Figure 5:
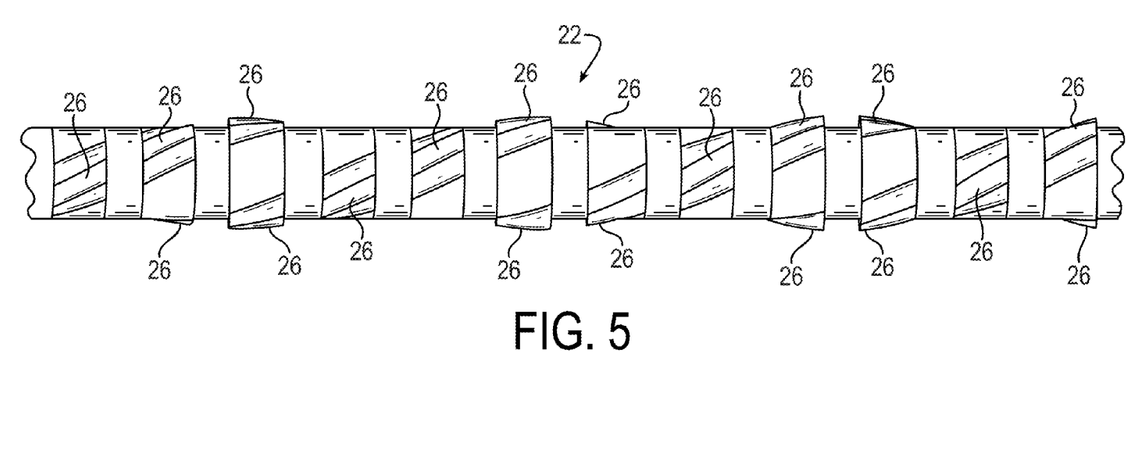
FIG. 5 is a photographic depiction of the central core and feature shown in FIG. 4.
Figure 6:
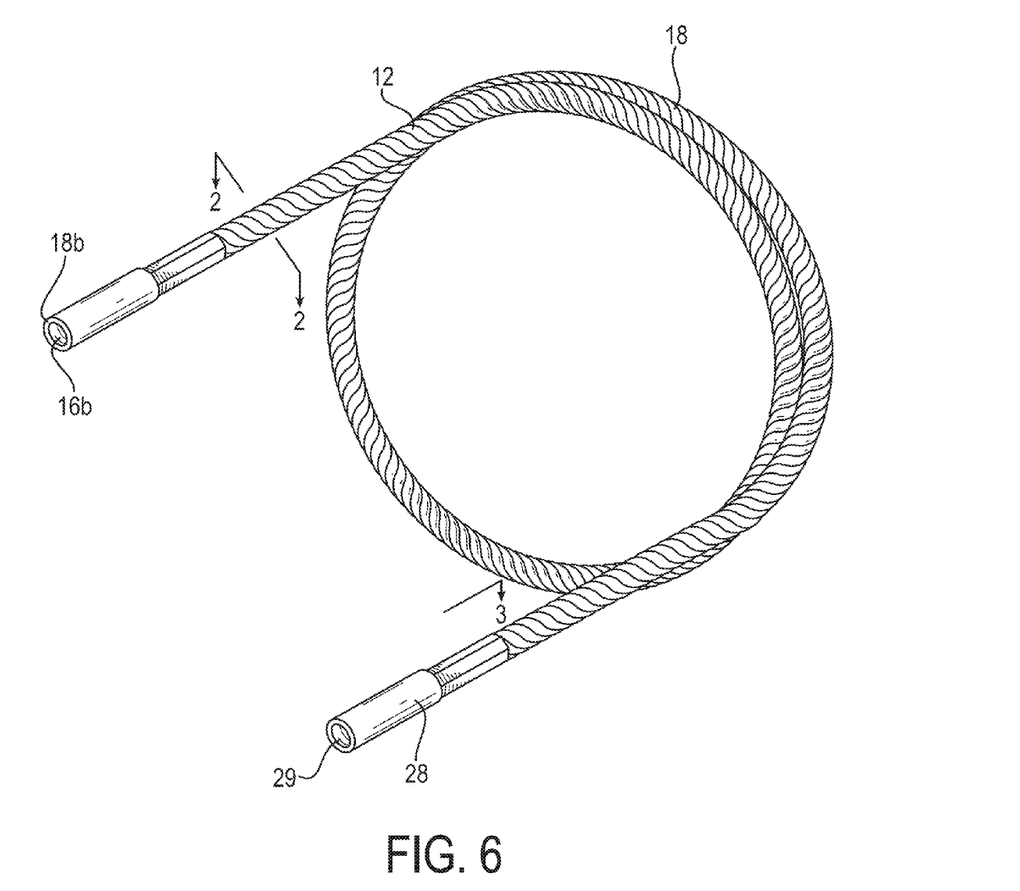
FIG. 6 depicts an embodiment of a central member having fittings on the leading and trailing ends thereof in a coiled position.

With reference to FIGS. 4A and 4B, a region 22 of central member 18 is provided with one or more attached feature 24 (or plurality of features 24) formed of a polymer. The leading end 23 of the region 22 of the overmolded material may have a tapered form to reduce the likelihood of the leading end catching on debris, accumulated deposits, rifling within a barrel or a joint between adjoining sections of pipe or other tubular members, and the tool 10 is threaded or pulled through the tubular member in the direction of the arrow in FIG. 4B. Feature 24 is preferably formed of a thermosetting rubber polymer by injection overmolding onto the central member 18. A wide variety of thermoplastic elastomers may be used. In one preferred embodiment the thermoplastic elastomer has a Shore A durometer hardness of approximately 60. Each feature 24 extends at least partially, and preferably fully, around central member 18 and radially distends the overlying region of sheath 12 to approximately the diameter of any specific caliber gun barrel, or range of gun barrel calibers, that tool 10 is intended to clean. Depending on the presence and/or thickness of the sheath and the elasticity of the polymer, the outer diameter of the protrusions may be slightly less than or slightly greater than the diameter of the barrel or other tubular member intended to be cleaned by the tool. Successive features 24 are preferably disposed in progressive angular rotation about central member 18. Each feature 24 is provided with at least one, and preferably two, radial protrusions 26. Preferably, feature 24 is provided as a plurality of substantially similar sub-features 24 helically oriented around central member 18 such that successive protrusions 26 urge the overlying fibers of sheath 12 to engage and follow the rifling lands in the barrel inner surface. The resulting twisting action imparted to sheath 12 provides superior cleaning of both the leading and trailing sides of each rifling land. The orientation of helical protrusions may be in either the same direction as or counter to the rifling of the gun barrel. The preferred helical orientation of the protrusions reduces the incidence of excess accumulations of dislodged residue forming along an annular protrusion that might otherwise result in jamming of the tool within a barrel or other tubular member. The region of the central member provided with protrusions may be adjacent the leading edge, the trailing edge or the middle portion of the tool. In another aspect of the invention, the tool may include more than a single portion provided with protrusions.

Central member 18 may comprise any material or elongate form, e.g., fiber rope or cord, rod, wire, or twisted or braided cable and may be rigid, semi-rigid or semi-flexible. The rigid or semi-rigid structure of tool 10 makes it an excellent gun barrel obstruction remover. It is preferable for the central member to have sufficient rigidity to be easily threaded or passed through the tubular member. A currently preferred material and form are a cable formed of a metal such as galvanized steel, preferably formed to have a natural curl for ease of laterally coiling in storage and preferably having a protective plastic coating. The protective plastic coating reduces the risk of scratching gun components and the potential for fraying of the cable. With respect to the cleaning of tubular members other than gun barrels, a semi-rigid structure of the core may accommodate some slight or eventual curves in the interior of a pipe, conduit or tube. However, a semi-flexible core member is preferable for cleaning sections of pipe, conduit or tubes having substantially curved shapes and turns between straight segments of tubular members.

Figure 7:
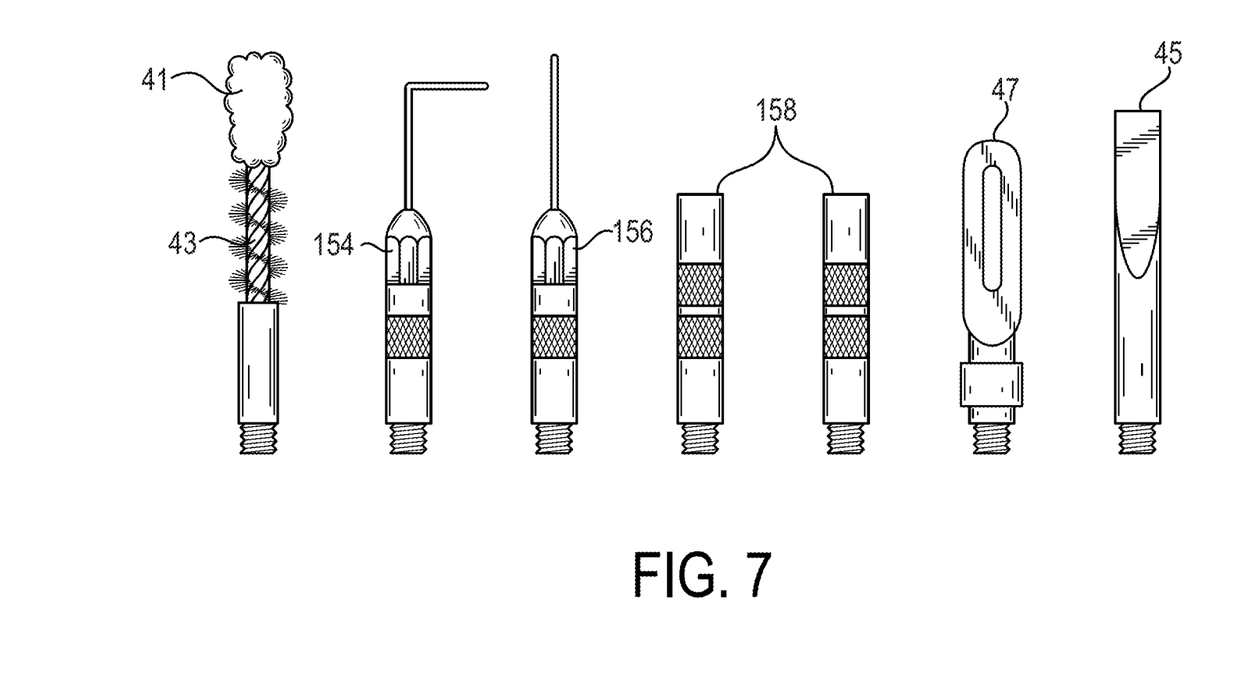
FIG. 7 depicts an assortment of typical auxiliary tools adapted to attach to the fittings at the end of the central member.
Figure 9A:
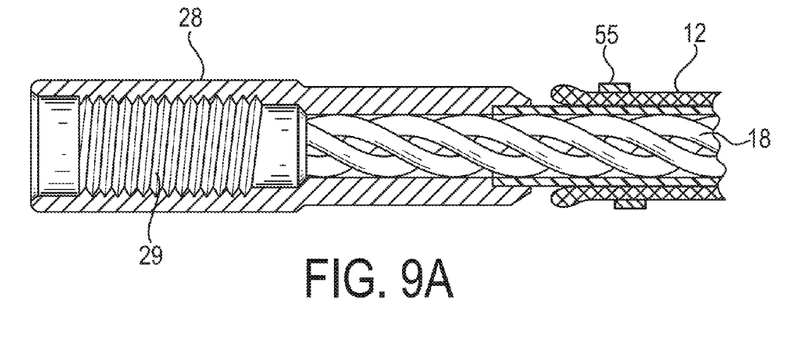
FIG. 9a depicts a crimping ring retaining the tubular woven sheath on the central member.
Figure 9B:
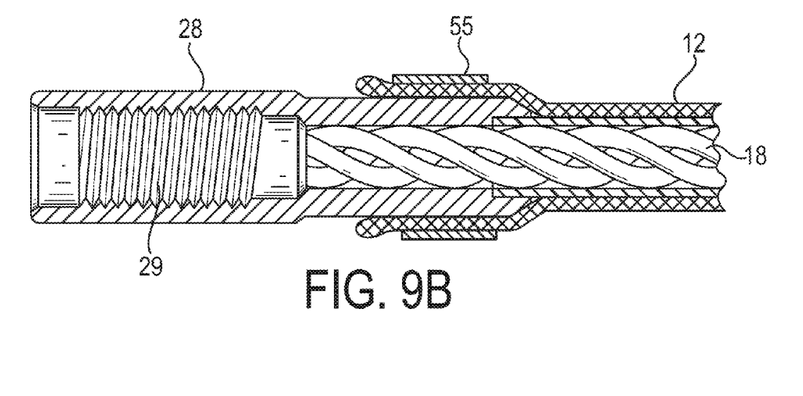
FIG. 9b depicts another embodiment wherein the crimping ring retains the sheath against a fitting at the end of the central member.

With reference to FIGS. 7, 9a and 9b, central member 18 preferably includes a fitting 28 at one end, and preferably at both ends, for attachment to any of various auxiliary tools such as swabs 41, brushes 43, scrapers 45, tips 47, a T-handle 51, and the like, as well as a cable extender and/or serially connection additional gun barrel cleaning tools 10. The fittings may be crimped, bonded or cold welded to the end of the central member. The fittings 28 may have internal or external threads 29 or other quick connect mechanisms to couple with the fittings of the auxiliary tools as depicted in FIG. 7.

In one aspect of the invention, the fittings 28 may also be sized and configured to attach one or both of the leading or trailing end of the sheath to the central member. Alternatively, as depicted in FIGS. 9a and 9b, a separate crimping ring 55 or other suitable connector may be utilized over the sheath 12 and the central member 18 or the fitting 28 to retain the edge of the sheath in place over the central core 18, overmolded protrusions 26 and absorbent material 53.

In another aspect of the invention, the sheath 12 is not connected to the fittings or central member 18, but held in place by the tight fit of the woven sheath 12 over the protrusions 26. In another aspect, the sheath may be removable from the tool for cleaning to remove build-up of removed residue. The sheath 12 may include elasticized threads to assist in the removal, cleaning and/or replacement of the sheath. Alternatively, cleaning may be accomplished by soaking the coiled tool in a suitable detergent solution and rinsed to remove the accumulated build-up of dislodged residue.

Preferably, sheath 12 is woven of primarily a natural fiber such as cotton, although synthetic fiber may be included; and 100% synthetic fiber is fully comprehended by the invention. Many natural fibers are sufficiently absorbent to retain adequate amounts of cleaning solvent without the need for sections of additional absorbent sponges between the sheath and the core. Additional special-purpose threads, such as fiber-optic 12a, phosphorescent or luminescent threads 12b, may also be woven into the sheath to provide, for example, auxiliary lighting for visual inspection of a gun barrel for cleanliness as tool 10 is withdrawn. In another aspect of the invention, the woven sheath may comprise fibers of heat resistant materials, such as meta-aramids, NOMEX, para-aramids, KEVLAR, fiberglass, K-fiber, or the like. In another aspect of the invention, synthetic fibers, such as nylon, polystyrene, acetals, acrylics or the like, or metallic thread, such as brass or the like, may be incorporated into the sheath to increase the abrasive characteristic of the sheath to assist in removal stubborn residue from the barrel. Sheath 12 may be woven, for example, on a tubular commercially available braiding machine In another aspect of the invention, where the sheath is comprised of heat resistant fibers or materials, cleaning of the sheath could be performed by the application of sufficient heat to burn off the accumulated reside. For example, the tool 10 or the sheath 12 could be placed in an over at a temperature below the melting or deformation temperature of the fibers such that any dirt or carbon residue detaches from the fibers of the sheath.

Figure 8:
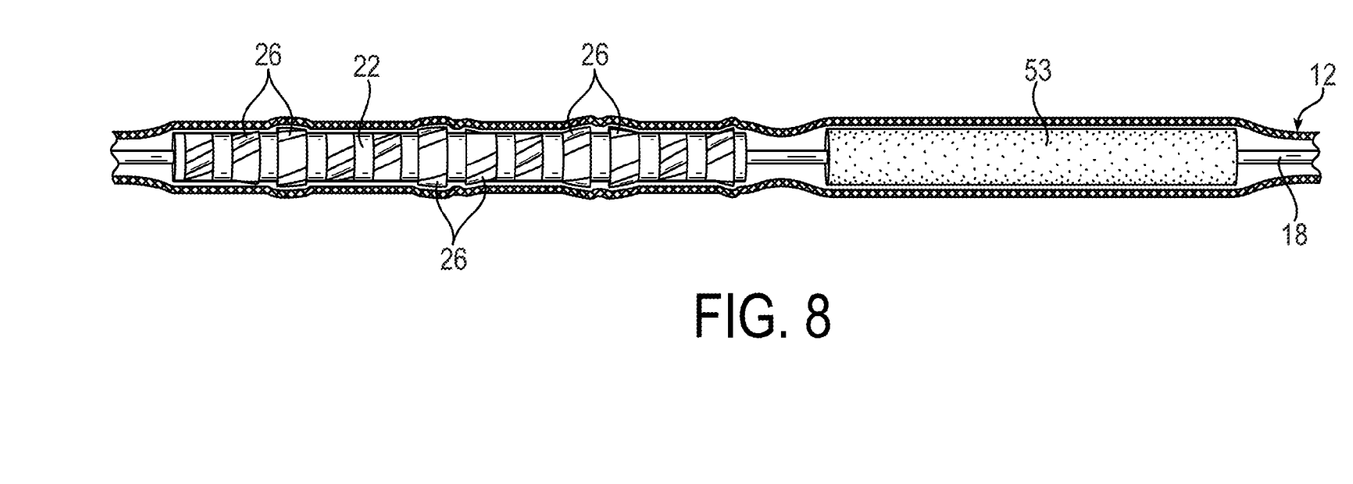
FIG. 8 depicts a cylindrical section of sponge or other absorbent material.

Preferably, additional absorbent material, such as a thin cylindrical sponge 53 may disposed about the central member and may be placed between the central member and the sheath. In one embodiment, at least one section of absorbent material is disposed about the central member at the lead end thereof, ahead of overmolded thermoplastic region 22 to assist in the application of cleaning solvent to the accumulated deposits or residue within a gun barrel. In another aspect of the invention, a second area of sponge material is disposed within the sheath adjacent to trailing end thereof to apply an even coating of lubricant or other corrosion resistant fluid. The absorbent material may hold additional solvent or lubricant that is applied as the gun barrel cleaner is pulled through the barrel. In another aspect of the invention, the natural fibers of the sheath or woven sheath are sufficiently absorbent to apply sufficient amounts of solvents and/or lubricants during the passing of the cleaner through the gun barrel in a single pass or multiple passes.

In another aspect of the invention, the gun barrel cleaner 10 may include successive or alternating areas of overmolded protrusions 26 and/or absorbent materials 53 to perform multiple cleaning operations in a single pass of the cleaner. For example, a first area of absorbent material is disposed closer to the leading end of the cleaner to apply a cleaning solvent. A second area of absorbent material is disposed adjacent to the trailing end of the gun barrel cleaner to apply a layer of protective lubricant. In between the areas of absorbent material, at least one area of overmolded protrusions is disposed to clean or abrasively scrub the interior of the gun barrel.

In another aspect of the invention, two sections of the gun barrel cleaner may be connected through a complementary fitting and/or adapter to clean longer gun barrels. In another aspect of the invention, two sections may be connected to complementary fittings at each end of an appropriately sized bore brush where additional abrasive force may need to be supplied.

In another aspect of the invention, the gun cleaning tool may be used to preserve the gun during storage. Preferably, when used for such purposes, the tool will include at least two areas of either overmolded thermoplastic elastomer or absorbent materials at intervals that approximate the overall length of the gun barrel. At least a portion of the sheath between two areas is treated with a vapor corrosion inhibitor. Alternatively, the vapor corrosion inhibitor could be molded or extruded within the plastic protective coating of the central member or the fibers of the sheath. When the tool is stored within the barrel for extended periods of time, the vapor corrosion inhibitor will off-gas to line the interior of the gun barrel with a protective coating to resist corrosion. The two overmolded or absorbent areas will fit relatively tightly within the barrel to retain the off-gassed corrosion inhibitor within the barrel to protect the barrel from corrosion.

Figure 3:
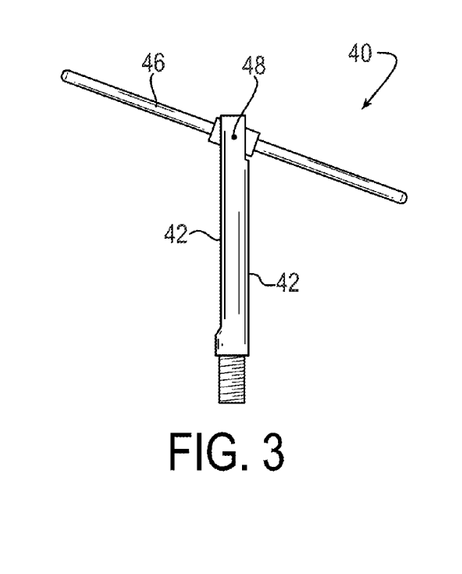
FIG. 3 is an elevational view of a foldable T-handle, also referred to interchangeably herein as a "pull-through handle tool", formed for passage in folded configuration through the barrel of a weapon.

Referring now to FIG. 3, an exemplary foldable T-handle 40, comprising a threaded shaft 42 having a longitudinal well 44 and a pivotable handle 46 attached to shaft 42 by pin 48 formed for passage in folded configuration through the bore of a weapon, is attachable to either of fittings 28, either before or after passage through a gun barrel of a leading end of apparatus 10, to assist a user in pulling apparatus 10 through a gun barrel. Where embodiments of the invention are used to clean the interior of tubular members having curved shapes, the T-handle is preferably attached to the fitting at the leading end of the central member after it is threaded through the tubular member. Where the interior of the tubular member is straight, a slim profile T-handle may be attached to the fitting at the leading end of the central member, or may be integrated with the fitting at the leading end of the central member. An exemplary slim profile T-handle is disclosed in U.S. patent application Ser. No. 13/448,973 entitled "Firearm Pull-Through Cleaning Tool with Integrated Foldable Handle," filed on Apr. 17, 2012 assigned to the common assignee of this application, which is hereby incorporated by reference in its entirety.

The respective thicknesses of the central core, protective layer, overmolded protrusions, absorbent materials and the woven sheath may be varied to change the radial width of the tool to fit the gun barrels of differing calibers. Alternatively, the compressibility of the overmolded protrusions, absorbent material and/or the woven sheath may also be increased so that a single tool may appropriately clean a range of calibers of gun barrels.

In another aspect of the invention, the natural fibers of the sheath and any absorbent material disposed beneath the sheath or at the trailing end of the central member may be used to absorb and remove spent cleaning fluids containing dislodged residue. However, the overmolded thermoplastic region has been successfully deployed to clean a variety of relatively narrow tubular members without a sheath. The plurality of protrusions, including particularly, a pair of the helical protrusions, formed around the overmolded thermoplastic region is effective at removing liquids and semi-solids such as grease and congealed oils, from narrow drains. The plurality of protrusions wipe excess accumulations of liquids and semi-solids in the manner of a squeegee from the interior of a pipe or drain. Even where a pipe or drain includes a catch or other curved portion, embodiments of the invention utilizing a semi-flexible central member were threaded through the drain and pulled through the tubular member. This embodiment removed excess accumulations of grease and spent oils in a small fraction of the time of other common methods.

While the present invention has been described with reference to a number of specific aspects or embodiments, it will be understood that the true spirit and scope of the invention should be determined only with respect to claims that can be supported by the present specification. While the particular embodiments may have been described in relation to cleaning the interior of a gun barrel, individuals skilled in the art will recognize and understand that the disclosure and embodiments herein are equally applicable to cleaning pipes, drains, conduits and tubing that is both straight and curved. Further, while in numerous cases herein wherein systems and apparatuses and methods are described as having a certain number of elements it will be understood that such systems, apparatuses and methods can be practiced with fewer than the mentioned certain number of elements. Also, while a number of particular embodiments have been described, it will be understood that features and aspects that have been described with reference to each particular embodiment can be used with each remaining particularly described embodiment.

What is claimed is:

1. A device for cleaning the barrel of a firearm having rifling lands comprising:
   a central member defining a core and having a longitudinal length, a leading end and a trailing end;
   a tubular woven sheath surrounding said central member and having a lead end and a trailing end; and
   at least five annular thermoplastic elastomer features disposed around said central member and spaced apart along the longitudinal length of the central member such that each feature is adjacent to another of said features, each of said features comprising at least one radial protrusion helically oriented around said central member, all of said radial protrusions having a same helical direction and substantially a same helix angle, and the radial protrusions of adjacent features being disposed in a progressive angular rotation relative to the central member such that said radial protrusions collectively form at least one discontinuous helix having discontinuities defined by a longitudinal space between each pair of adjacent features, wherein the radial protrusions of successive features urge a plurality of overlying fibers of said tubular woven sheath to engage and follow the rifling lands of an inner surface of said barrel of said firearm, and wherein the tubular woven sheath is held in place by a tight fit of the tubular woven sheath over the radial protrusions.

2. The device for cleaning the barrel of a firearm according to claim 1 wherein said central member is selected from the group consisting of rope, cord, rod, wire, twisted cable, and braided cable.

3. The device for cleaning the barrel of a firearm according to claim 1 wherein said central member is a metal cable.

4. The device for cleaning the barrel of a firearm according to claim 1 wherein said central member further comprises a protective coating.

5. The device for cleaning the barrel of a firearm according to claim 3 wherein said central member has a fitting at one end adapted to attach an auxiliary tool selected from the group consisting of brushes, scrapers, tips, swabs, handles, adapters and extender cables.

6. The device for cleaning the barrel of a firearm according to claim 1 wherein said tubular woven sheath comprises a natural fiber.

7. The device for cleaning the barrel of a firearm according to claim 1 wherein said tubular woven sheath further comprises a fiber of abrasive materials selected from the group consisting of nylon, polystyrene, acetals, acrylics, and brass.

8. The device for cleaning the barrel of a firearm according to claim 1 wherein said tubular woven sheath comprises heat resistant materials selected from the group consisting of meta-aramids, NOMEX, para-aramids, KEVLAR, fiberglass, and K-fiber.

9. The device for cleaning the barrel of a firearm according to claim 1 wherein said tubular woven sheath includes a fiber selected from the group consisting of fiber-optic, luminescent and phosphorescent to provide for auxiliary lighting for visual inspection of said barrel of a firearm.

10. The device for cleaning the barrel of a firearm according to claim 1 wherein the tubular woven sheath further comprises elasticized threads to assist in the removal and replacement of the tubular woven sheath over the central member and the radial protrusions.

11. The device for cleaning the barrel of a firearm according to claim 1 wherein an outer diameter of said radial protrusions are approximately equal to a diameter of the bore of the barrel of a firearm.

12. The device for cleaning the barrel of a firearm according to claim 1 wherein said radial protrusions are formed by overmolding onto said central member.

13. The device for cleaning the barrel of a firearm according to claim 1 wherein the radial protrusions form discontinuous ridges.

14. The device for cleaning the barrel of a firearm according to claim 1 wherein the helical orientation of said radial protrusions is in the same direction as said rifling lands within said gun barrel.

15. The device for cleaning the barrel of a firearm according to claim 1 wherein said central member is formed with a natural curl to promote laterally coiling in storage.

16. The device for cleaning the barrel of a firearm according to claim 1 further comprises absorbent material disposed between said central member and said tubular woven sheath.

17. The device for cleaning the barrel of a firearm according to claim 1 further comprising a crimping ring to attach the sheath to the central member.

18. The device for cleaning the barrel of a firearm according to claim 1 wherein the crimping ring retains a leading edge of the sheath in place over the central member.

* * * * *